United States Patent [19]

Gruber

[11] Patent Number: 6,100,429
[45] Date of Patent: Aug. 8, 2000

[54] N-BENZYLIDENE AMINOPHENYLACETYLENE CARBINOLS

[75] Inventor: John M. Gruber, Mountain View, Calif.

[73] Assignee: Catalytica Pharmaceuticals, Inc., Mountain View, Calif.

[21] Appl. No.: 09/334,100

[22] Filed: Jun. 16, 1999

Related U.S. Application Data

[62] Division of application No. 08/892,278, Jul. 14, 1997, abandoned.

[51] Int. Cl.$^7$ .................................................. C07C 251/24
[52] U.S. Cl. ........................... 564/275; 560/35; 560/138; 562/440; 564/15; 564/221; 564/272; 564/273; 564/274; 564/443
[58] Field of Search ..................................... 564/272, 275, 564/443, 273, 274, 15, 221; 560/35, 138; 562/440

[56] References Cited

U.S. PATENT DOCUMENTS

| | | | |
|---|---|---|---|
| 4,128,588 | 12/1978 | Sabourin et al. | 260/645 |
| 4,139,561 | 2/1979 | Onopchenko et al. | 260/575 |
| 4,204,078 | 5/1980 | Sabourin et al. | 568/705 |
| 4,215,226 | 7/1980 | Onopchenko et al. | 568/705 |
| 4,216,341 | 8/1980 | Onopchenko et al. | 568/705 |
| 4,219,679 | 8/1980 | Onopchenko et al. | 568/705 |

FOREIGN PATENT DOCUMENTS 0 131 968    1/1985    European Pat. Off. .

OTHER PUBLICATIONS

Wright et al. I, Chem. Abstr. 124:102588, 1995.
Wriight et al. II, Chem. Abstr. 124:30462, 1995.
Whittall et al., 'Organometallic Complexes for Nonliner Optics, etc.', Organomettalics, 15, 1935–41, Apr. 1996.

Sabourin, "A New Synthesis of Meta–Aminophenylacetylene", Prepr. Div. Pet. Chem., Am. Chem. Soc., vol. 24 (1979), pp. 233–239.

Onopchenko et al., "Selective Catalytic Hydrogenation of Aromatic Nitro Groups in the Presence of Acetylenes. Synthesis of (3–Aminophenyl)acetylene via Hydrogenation of Dimethylcarbinol Substituted (3–Nitrophenyl)acetylene over Heterogeneous Metallic Ruthenium Catalyst", J. Org. Chem., vol. 44, No. 8, (1979) pp. 1233–1236.

Onopchenko et al., "Selective Catalytic Hydrogenation of Aromatic Nitro Groups in the Presence of Acetylenes. Synthesis of (3–Aminophenyl)acetylene via Hydrogenation of (3–Nitrophenyl)acetylene over Cobalt Polysulfide and Ruthenium Sulfide Catalysts", J. Org. Chem., vol. 44, No. 21, (1979) pp. 3671–3674.

Bleicher et al., "Aryl– and Heteroaryl–Alkyne Coupling Reactions Catalyzed by Palladium on Carbon and CuI in an Aqueous Medium", Synlett, (1995) pp. 1115–1116.

*Primary Examiner*—Peter O'Sullivan
*Attorney, Agent, or Firm*—John H. Grate

[57] ABSTRACT

This invention provides a process for preparing aminoarylacetylenes comprising reacting a N-arylmethylidene aminoarylhalide with a terminal acetylene in the presence of a base and a catalyst system comprising a palladium catalyst and a cuprous salt to produce a novel N-arylmethylidene aminoarylacetylene, and hydrolyzing the N-arylmethylidene aminoarylacetylene to the aminoarylacetylene. In one embodiment, the invention provides a process for preparing aminophenylacetylenes comprising reacting a N-benzylidene aminophenylhalide with a terminal acetylene in the presence of a base and the catalyst system to produce a novel N-benzylidene aminophenylacetylene, and hydrolyzing the N-benzylidene aminophenylacetylene to the aminophenylacetylene

4 Claims, No Drawings

N-BENZYLIDENE AMINOPHENYLACETYLENE CARBINOLS

This application in a divisional of U.S. Ser. No. 08/892,278 filed Jul. 14, 1997, now abandoned.

FIELD OF THE INVENTION

This invention relates generally to preparing aminoarylacetylenes. More specifically, it relates to preparing aminoarylacetylenes from aminoarylhalides and terminal acetylenes and to novel compounds which are useful in their preparation. Aminophenylacetylenes are valuable as precursors to pharmaceutically active compounds and to acetylene terminated polymers. In particular, 3-aminophenylacetylene is used as an end-capping agent for high performance polyimide resins.

BACKGROUND OF THE INVENTION

Sabourin, *Prepr. Div. Pet. Chem., Am. Chem. Soc.*, vol. 24, pp. 233–239 discloses the preparation of 2-methyl-4-(3-aminophenyl)-3-butyn-2-ol (an aminophenylacetylene) and 3-aminophenylacetylene in two and three steps, respectively, from 3-bromonitrobenzene and 2-methyl-3-butyn-2-ol. In the first step, 3-bromonitrobenzene and 2-methyl-3-butyn-2-ol were reacted in the presence of a catalyst system of bis(triphenylphosphine)palladium dichloride, additional triphenylphosphine, and cuprous iodide in triethylamine solvent at the reflux temperature to obtain 2-methyl-4-(3-nitrophenyl)-3-butyn-2-ol. In the second step, this nitrophenylacetylene was hydrogenated in isopropanol in the presence of a $Ru/Al_2O_3$ catalyst to obtain 2-methyl-4-(3-aminophenyl)-3-butyn-2-ol. This reference states that is essential to stop the hydrogenation reaction at the stoichiometric point because reduction of the triple bond ensues. In the third step, this aminophenylacetylene was heated in toluene in the presence of sodium hydroxide pellets, with removal of the acetone co-product by distillation, to obtain 3-aminophenylacetylene.

This reference also discloses an attempt to similarly react 3-bromoaniline, instead of 3-bromonitrobenzene, with 2-methyl-3-butyn-2-ol to obtain 2-methyl-4-(3-aminophenyl)-3-butyn-2-ol directly, and reports that 3-bromo-aniline failed to react at any appreciable rate at temperatures up to ca. 100° C.

U.S. Pat. Nos. 4,128,588 and 4,204,078 (each also from the same Sabourin as inventor, with Selwitz) also discloses this preparation of 2-methyl-4-(3-nitrophenyl)-3-butyn-2-ol from 3-bromonitrobenzene and 2-methyl-3-butyn-2-ol. U.S. Pat. No. 4,139,561 and *J. Org. Chem.*, vol. 44 (1979), pp. 1223–1236 (both Onopchenko as well as the same Sabourin and Selwitz) also discloses the preparation of 2-methyl-4-(3-aminophenyl)-3-butyn-2-ol from 2-methyl-4-(3-nitrophenyl)-3-butyn-2-ol by hydrogenation with a ruthenium catalyst, and its subsequent conversion to 3-aminophenylacetylene. Both the patent and journal disclosures highlight the difficult challenge of selectively hydrogenating the nitro group in the presence of the acetylene group. Subsequent U.S. Pat. Nos. 4,215,226; 4,216,341; 4,219,679 and a publication *J. Org. Chem.*, vol. 44 (1979), pp. 3671–3674 from Onopchenko, Sabourin, and Selwitz disclose hydrogenations of 2-methyl-4-(3-nitrophenyl)-3-butyn-2-ol to 2-methyl-4-(3-aminophenyl)-3-butyn-2-ol using other hydrogenation catalysts.

Synlett, 1995, pp. 1115–1116 discloses this preparation of 2-methyl-4-(4-nitrophenyl)-3-butyn-2-ol from 4-bromonitrobenzene and 2-methyl-3-butyn-2-ol in high yield using a catalyst system comprising palladium on carbon, triphenylphosphine, and cuprous iodide in the presence of 2.5 equivalents of potassium carbonate in 1:1 1,2-dimethoxyethane:water at 80° C. This reference also discloses the preparation of 2-methyl-4-(3-aminophenyl)-3-butyn-2-ol in 78% isolated yield from 3-iodoaniline (in place of 4-bromonitro-benzene) using the same system and the same conditions. The reference does not disclose any attempt to similarly react 3-bromoaniline.

OBJECTS OF THE INVENTION

The object of this invention is to provide an economically preferable, effective and efficient process for the preparation aminophenylacetylenes. A further object of this invention is to provide a process for the preparation of aminophenylacetylenes that avoids the inherent challenge of selectively hydrogenating a nitro group in the presence of an acetylene group. Another object of this invention is to provide a process for the preparation of aminophenylacetylenes from aminophenylhalides. The present invention is directed towards one or more of the above objects. Other objects and advantages will become apparent to persons skilled in the art and familiar with the background references from a careful reading of this specification.

SUMMARY OF THE INVENTION

In its most general terms, the present invention provides a process for preparing aminoarylacetylenes comprising reacting an N-arylmethylidene aminoarylhalide with a terminal acetylene in the presence of a base and a catalyst system comprising a palladium catalyst and a cuprous salt to produce a novel N-arylmethylidene aminoarylacetylene. The N-arylmethylidene aminoarylacetylene may be hydrolyzed to remove the N-arylmethylidene group and provide the aminoarylacetylene. The present invention thereby provides a practical process for preparing an aminophenylacetylene comprising reacting a N-benzylidene aminophenylhalide with a terminal acetylene in the presence of a base and a catalyst system comprising a palladium catalyst and a cuprous salt to produce a novel N-benzylidene aminophenylacetylene, and hydrolyzing the N-benzylidene aminophenylacetylene to the aminophenylacetylene. N-benzylidene aminophenylhalides can be readily prepared from the corresponding benzaldehyde and the corresponding aminophenylhalide by methods known in the art, typically in the presence of an acid catalyst. In certain embodiments of the present invention, the N-benzylidene aminophenylhalide is provided in the reaction by the benzaldehyde, the aminophenylhalide, and an acid catalyst. The invention thereby provides a process for the preparation of aminophenylacetylenes from aminophenylhalides that avoids the inherent challenge of selectively hydrogenating a nitrophenylacetylene to an aminophenylacetylene.

From experiments using a substoichiometric amount of benzaldehyde relative to the aminophenylhalide, it was surprisingly discovered that the remaining free aminophenylhalide in the mixture with the resulting N-benzylidene aminophenylhalide also reacts, providing a mixture of the aminophenylacetylene and the N-benzylidene aminophenylacetylene. Apparently, the substoichiometric amount of the benzylidene group catalyzes the conversion of aminophenylhalide to the aminophenylacetylene. While not intending to be bound by theory, this can be explained by the benzylidene group being transferred, during the reaction, from the initial product, the N-benzylidene aminophenylacetylene, to the unreacted free aminophenylhalide, converting it to the more reactive N-benzylidene aminophenylhalide.

In one preferred embodiment, the present invention provides a process for the preparation of 3-aminophenylacetylene carbinols from 3-aminophenyl-halides comprising reacting a N-benzylidene derivative of the 3-aminophenyl-halide with a alpha-hydroxy terminal acetylene in the presence of an amine base and a catalyst system comprising a palladium catalyst comprising a phosphorus ligand and a cuprous halide, and hydrolyzing the resulting novel N-benzylidene 3-aminophenylacetylene carbinol to the 3-aminophenyl-acetylene carbinol. Optionally, a mixture of the 3-aminophenylhalide and the N-benzylidene 3-aminophenylhalide is reacted to provide a mixture of the 3-aminophenylacetylene carbinol and the corresponding N-benzylidene aminophenylacetylene carbinol. 3-amino-phenylacetylene carbinols may be converted to 3-aminophenylacetylene by methods known in the art. The invention thereby provides an efficient process for the preparation of 3-aminophenylacetylene from 3-aminophenylhalides.

DETAILED DESCRIPTION OF THE INVENTION

Suitable starting materials and intermediates for the preparation of aminoarylacetylenes by the present invention are aminoarylhalides in general, arylcarboxaldehydes in general, terminal acetylenes in general, N-arylmethylidene aminoarylhalides in general, and N-arylmethylidene aminoarylacetylenes in general. The N-arylmethylidene aminoarylhalide and the N-arylmethylidene aminoarylacetylene may be cis isomers or trans isomers, or mixtures thereof, about the carbon-nitrogen double bond.

Suitable aminoaryl groups for the aminoarylhalide, the N-aryl-methylidene aminoarylhalide, the N-arylmethylidene aminoarylacetylene, and the aminoarylacetylene include those in which the aryl ring system is a carbocyclic aromatic ring system, having only carbon atoms in the ring system, and those in which the aromatic ring system is a heterocyclic aromatic ring system, having one or more heteroatoms in the ring system. Typical carbocyclic aromatic ring systems in the aminoaryl group have 6–14 carbon atoms in the aromatic ring system. Preferred carbocyclic aromatic ring systems are phenyl and substituted phenyl groups. Suitable heterocyclic aromatic ring systems in the aminoaryl group have 5–13 atoms in the aromatic ring system which comprises carbon atoms and one or more heteroatoms. Preferred heteroatoms are oxygen, sulfur, and nitrogen. Typical heterocyclic aromatic ring systems have 5 or 6 atoms in an aromatic ring comprising one or more heteroatoms selected from the group oxygen, sulfur, and nitrogen, benzfused derivatives thereof, and substituted derivatives thereof. Examples of preferred heterocyclic aromatic ring systems in the aminoaryl group include pyridyl, furyl, thienye, pyrrolyl, their benz-fused derivatives quinolinyl, isoquinolinyl, benzfuryl, benzothienye, indolyl, isoindolyl, and substituted derivatives thereof.

Suitable aryl groups for the arylmethylidene group of the arylcarboxaldehyde, the N-arylmethylidene aminoarylhalide, and the N-arylmethylidene aminoarylacetylene include those having the aromatic ring systems described above as suitable for the aminoaryl group. (An arylcarboxaldehyde is an arylmethylidene oxide. For example, benzaldehyde is benzylidene oxide and is phenylcarboxaldehyde and is phenylmethylidene oxide.) The aromatic ring system in the arylmethylidene group may be the same or different from the aromatic ring system in the aminoaryl group.

For the preparation of aminophenylacetylenes via N-benzylidene aminophenylhalides, suitable starting materials and intermediates are aminophenylhalides in general, benzaldehydes in general, terminal acetylenes in general, N-benzylidene aminophenylhalides in general, and N-benzylidene aminophenylacetylenes in general. Suitable aminophenylhalides, benzaldehydes, terminal acetylenes, N-benzylidene aminophenylhalides, and N-benzylidene aminophenylacetylenes include those having the structural formulas I, II, III, IV, and V, respectively. The aminophenylacetylenes prepared from these suitable starting materials and intermediates have the structural formula VI.

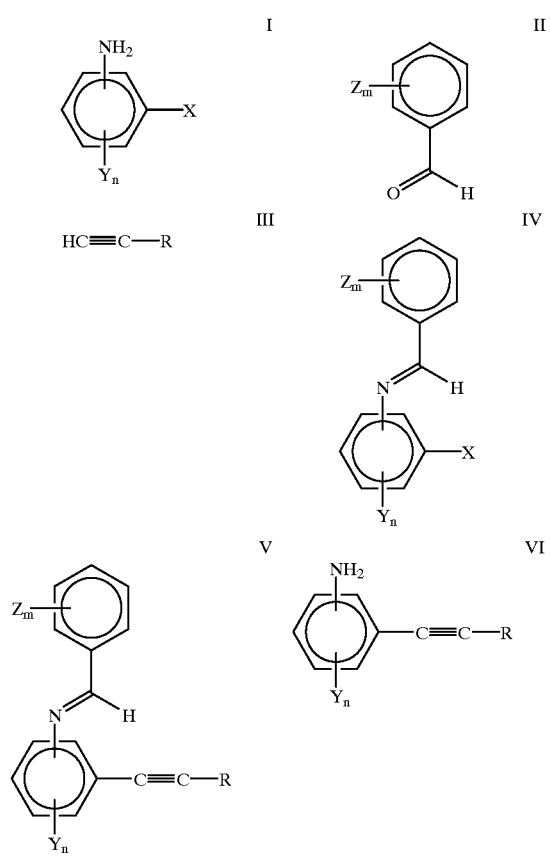

X in formulas I and IV is a halogen substituent selected from the group consisting of chloro, bromo, and iodo, preferably selected from the group bromo and iodo, and most preferably bromo.

Y in formulas I, IV, V and VI is a substituent selected from substituents that do not interfere with the reaction chemistry of the invention. These are known to persons skilled in the art and can be determined by routine experimentation. Examples of suitable substituents include fluoro, chloro (provided X is bromo or iodo), alkyl (preferably $C_1$–$C_{12}$), alkenyl (preferably $C_1$–$C_{12}$), alkynyl (preferably $C_1$–$C_{12}$), alkoxy (preferably $C_1$–$C_{12}$), acyloxy (preferably $C_1$–$C_{12}$), aryl, aryloxy, heteroaryl, OH, $NO_2$, CN, COOH, $SO_2R$, SOR, $NH_2$, NH-alkyl (preferably $C_1$–$C_{12}$), N-dialkyl (preferably $C_1$–$C_{12}$), trihalomethyl, NHCO-alkyl (preferably $C_1$–$C_8$), CONH-alkyl (preferably $C_1$–$C_4$), CON-dialkyl (preferably $C_1$–$C_4$), COO-alkyl (preferably $C_1$–$C_{12}$), $CONH_2$, CO-alkyl (preferably $C_1$–$C_{12}$), NHCOH, NHCOO-alkyl (preferably $C_1$–$C_8$), CO-aryl, COO-aryl, CHCHCO$_2$-alkyl (preferably $C_1$–$C_{12}$), CHCHCO$_2$H, PO-diaryl, and PO-dialkyl (preferably $C_1$–$C_8$).

The subscript n in the formulas I, II, IV, V, and VI is an integer from 0 to 4, preferably 0 or 1, and most preferably 0. When n=0, no substituent Y is present in the formula. When n is greater than 1, the Y substituents may be the same or different and are selected independently of each other.

Z in formulas II, IV, and V is defined as for Y above. The subscript m is an integer from 0 to 5, preferably 0 or 1, and most preferably 0. When m=0, no substituent Z is present in the formula. When m is greater than 1, the Z substituents may be the same or different and are selected independently of each other.

The N-benzylidene aminophenylhalides and N-benzylidene aminophenyl-acetylenes can be trans isomers (as shown in formulas IV and V) or cis isomers, or mixtures thereof, about the carbon-nitrogen double bond.

R in formulas III, V, and VI is hydrogen or any substituent that does not interfere with the reaction chemistry of the invention. These are known to persons skilled in the art and can be determined by routine experimentation. Examples of suitable substituents include alkyl (preferably $C_1$–$C_{12}$), alkenyl (preferably $C_1$–$C_{12}$), alkynyl (preferably $C_1$–$C_{12}$), alkoxy (preferably $C_1$-$C_1$–$C_{12}$), acyloxy (preferably $C_1$–$C_{12}$), aryl, aryloxy, heteroaryl, NH-alkyl (preferably $C_1$–$C_{12}$), N-dialkyl (preferably $C_1$–$C_{12}$), trihalomethyl, NHCO-alkyl (preferably $C_1$–$C_8$), CONH-alkyl (preferably $C_1$–$C_4$), CON-dialkyl (preferably $C_1$–$C_4$), COO-alkyl (preferably $C_1$–$C_l2$), CONH$_2$, CO-alkyl (preferably $C_1$–$C_{12}$), NHCOH, NHCOO-alkyl (preferably $C_1$–$C_8$), CO-aryl, COO-aryl, CHCHCO$_2$-alkyl (preferably $C_1$–$C_{12}$), and hydroxyalkyl (preferably $C_1$–$C_{12}$).

In a preferred embodiment, a N-benzylidene aminophenylhalide, optionally in mixture with additional aminophenylhalide, is reacted with a alpha-hydroxy terminal acetylene to provide the N-benzylidene aminophenylacetylene carbinol and, ultimately, the aminophenylacetylene carbinol. R in the alpha-hydroxy terminal acetylene, the N-benzylidene aminophenylacetylene carbinol and the aminophenylacetylene carbinol is a alpha-hydroxy-alkyl group of the formula -C(OH)R'R", as shown in formulas VII, VIII, and IX, respectively.

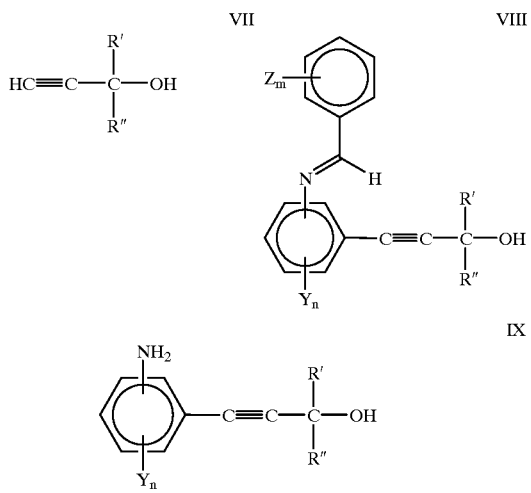

Y, n, Z and m in formulas VIII and IX are defined as above.

R' and R" in formulas VII, VIII, and IX can be the same or different and are defined as for R, above. Preferred R' and R" are independently selected from the group consisting of hydrogen, lower alkyl groups having from 1 to 4 carbon atoms, phenyl, substituted phenyl; or R' and R" when taken together with the carbon bearing the hydroxyl group form a saturated cycloalkyl group, preferably a cyclohexyl or cylopentyl group.

The preparation of the alpha-hydroxy terminal acetylenes is well known in the art. For example, acetylene can be reacted with acetone to form 2-methyl-3-butyn-2-ol (also known as acetylene dimethylcarbinol), which is a preferred alpha-hydroxy terminal acetylene for use in the process of this invention. Other suitable alpha-hydroxy terminal acetylenes include 3-methyl-1-pentyn-3-ol, 3-ethyl-1-pentyn-3-ol, 2-phenyl-3-butyn-2-ol, 1-ethynylcyclohexanol, and 1-ethynlcyclopentanol.

In the following detailed description of the process, the aminophenylhalide, the benzaldehyde, the N-benzylidene aminophenylhalide, the N-benzylidene aminophenylacetylene, and the aminophenylacetylene are used, as preferred embodiments, to describe the process for aminoarylhalides in general, arylcarboxaldehydes in general, N-arylmethylidene aminoarylhalides in general, N-arylmethylidene aminoarylacetylenes in general, and aminoarylacetylenes in general, respectively.

The N-benzylidene aminophenylhalides can be prepared by methods known in the art for preparing imines from anilines and benzaldehydes, typically in the presence of an acid catalyst. The N-benzylidene aminophenylhalide can be provided preformed to the reaction or can be prepared in solution for the reaction from the benzaldehyde, the aminophenylhalide, and an acid catalyst. The nature and amount of the acid catalyst is not critical provided it is effective to produce the N-benzylidene aminophenylhalides and does not interfere with the process to form the aminophenylacetylene, which can be determined by routine experimentation. Benzaldehydes from commercial sources often contain the corresponding benzoic acid as an impurity, and in many cases, this benzoic acid is all the acid that is needed to catalyze the formation of the N-benzylidene aminophenylhalides. Other carboxylic acids (e.g. acetic acid) also provide effective acid catalysts. Hydrohalic acids and amine hydrohalides may also be used. Solid acids, acid resins for example, may also be used.

When formed in the solution for reaction, the mole ratio of benzaldehyde to the aminophenylhalide is typically in the range 0.01:1 to 1.1:1, preferably in the range 0.1:1 and 1.0:1. When a mole ratio of 1.0:1 or greater is used, essentially all of the aminophenylhalide is converted to the N-benzylidene aminophenylhalide. When a mole ratio of less than 1.0:1 is used, a mixture of N-benzylidene aminophenylhalide and free aminophenylhalide is provided. Mixtures of N-benzylidene aminophenylhalide and free aminophenylhalide can also be provided using preformed N-benzylidene aminophenylhalide. The mole ratio of N-benzylidene aminophenylhalide to free aminophenylhalide in such mixtures, whether made using preformed N-benzylidene aminophenylhalide or made using the benzaldehyde is typically in the range 0.01:1 to 0.99:1, preferably in the range 0.1:1 to 0.9:1. As used herein, the term "aminophenylhalide reactant" refers to the N-benzylidene aminophenylhalide in combination with any free aminophenylhalide in mixture with it.

The ratio of the aminophenylhalide reactant to the terminal acetylene is not critical. Either reactant may be the limiting reactant and this choice can respond to other considerations, such as which is the more costly reactant to provide and which is more readily separated or removed to an acceptable level from the product. Generally the mole ratio of aminophenylhalide reactant to terminal acetylene is in the range 0.5:1 to 2:1. In typical embodiments, this ratio is in the range 1:1 to 1.5:1.

The reaction of the aminophenylhalide reactant with the terminal acetylene occurs in the presence of a base according to the following general reaction equation:

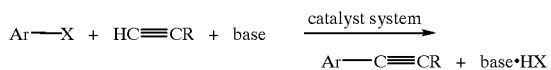

$$Ar\text{---}X + HC\equiv CR + base \xrightarrow{\text{catalyst system}} Ar\text{---}C\equiv CR + base\cdot HX$$

wherein Ar is the aminophenyl of the aminophenylhalide reactant, and X and R are as defined above. The identity of the base is not critical provided it is effective in the reaction and does not interfere with the reaction, which can be determined by routine experimentation. Suitable bases include amine bases, carboxylate salts, carbonate salts, and bicarbonate salts. Secondary and tertiary amine bases are preferred. Particularly preferred are dialkyl and trialkyl amines having the general formula $NR^aR^bR^c$, wherein $R^a$, $R^b$, and $R^c$ are independently selected from the group consisting of hydrogen and lower alkyl groups having from 1 to 4 carbons; or where two of $R^a$, $R^b$, and $R^c$ when taken together with the nitrogen form a heterocyclic amine; with the proviso that no more than one of $R^a$, $R^b$, and $R^c$ is hydrogen. Illustrative examples of such preferred amine bases include dimethylamine, trimethylamine, diethylamine, triethylamine, dibutylamine, tributylamine, and N-methylpiperidine. Most preferred are the trialkyl amines. Related amine bases that do not fit this formula precisely, such as N-methylmorpholine, N,N-dimethylaniline, and N,N-dimethylaminopyridine are also suitable. A combination of a soluble base (e.g. an amine base) and an insoluble base (e.g. a carbonate salt) may also be used.

The mole ratio of the base to the limiting reactant, whether the aminophenylhalide reactant or the terminal acetylene is typically at least 1.0. Higher ratios of base to the reactants are suitable. The preferred amine bases may be conveniently used as solvent for the reaction.

Suitable palladium catalysts include those provided by palladium compounds and salts, in particular palladium(0) compounds and palladium(II) compounds and salts. Preferably, the catalyst also comprises a ligand.

Suitable ligands include monodentate and bidentate ligands comprising nitrogen or phosphorus as ligating atom. Preferred ligands are triorganophosphine, triorganophosphite, and aromatic nitrogen heterocycle ligands. Examples of preferred ligands include triarylphosphines (e.g. triphenylphosphine), bidentate bis(diarylphosphino) compounds (e.g. 1,1'-bis-(diphenylphosphino)butane), trialkylphosphites (e.g. triisopropylphosphite), and pyridine-type ligands (e.g. pyridine, bipyridine). Particularly preferred are ligands are trioganophosphines having the general formula $PR^dR^eR^f$, wherein $R^d$, $R^e$, and $R^f$ are independently selected from the group consisting of alkyl groups having from 1 to 6 carbon atoms, phenyl, and substituted phenyl groups. The substituents on the phenyl groups can include alkyl groups having from 1 to 4 carbon atoms, alkoxy groups having 1 to 4 carbon atoms, and halogen. Triphenylphosphine is a frequently used preferred ligand.

Suitable and optimal ratios of the ligand to palladium depend on a number of other parameters, including the identity of the ligand, the concentration of the palladium catalyst, the reaction temperature, the reactivity of the reactants, the solvent, and the like, and can be readily determined by routine experimentation. Typically the mole ratio of the ligand to palladium is in the range of 1:1 to 100:1, preferably in the range 2:1 to 50:1, and most preferably in the range 4:1 to 20:1. In certain embodiments, improved conversion of the aminophenylhalide reactant and improved yield of the aminophenylacetylene is obtained by providing an amount of ligand in the reaction mixture in excess of the maximum mole ratio (4:1) that can be bound to the palladium.

The active palladium catalyst may be prepared in advance of its introduction to the reaction mixture, or may be generated in the reaction mixture. It is believed that the active catalyst in the reaction is a palladium(0) compound. The active palladium catalyst may be provided by a preformed ligated palladium(0) compound (e.g. tetrakis(triphenylphosphine)-palladium(0)), or may be provided by combining in solution, either ex situ or in situ to the reaction mixture, a suitable ligand with a suitable palladium(0) compound (e.g. tris(dibenzylideneacetone)palladium(0)). When the catalyst is provided by a palladium(II) compound or salt, the active catalyst is provided by its reduction either ex situ or in situ to the reaction mixture. Generally, the other components of the reaction mixture (e.g. an amine base) is capable of reducing the palladium(II) to generate the active catalyst in situ. This can be determined by routine experimentation. Suitable reductants for ex situ generation of the active catalyst from and palladium(II) sources are known in the art and include organomagnesium halide reagents (e.g. methylmagnesium halide) and various hydride reagents (e.g. sodium bis(2-methoxyethoxy)aluminum dihydride). Preferably the palladium(II) is combined with ligand prior to its reduction. The palladium(II) may be provided as a preformed ligated palladium(II) compound (e.g. dichlorobis(triphenyl-phosphine)palladium(II)) or may be provided by combining in solution a suitable ligand with a suitable palladium(II) compound (e.g. dichlorobis(acetonitrile)palladium(II)) or palladium(II) salt. Suitable palladium(II) salts include the salts having the general formula $PdA_2$, wherein A is an inorganic or organic salt anion. The identity of the anion A is not critical but it must not interfere with the reaction, which can be determined by routine experimentation. Preferred palladium(II) salts include the chlorides, bromides, carboxylates (e.g. formate, acetate, stearate) and acetylacetonates. Particularly preferred are palladium diacetate and palladium dichloride.

The amount of palladium catalyst is not critical, but should be a catalytic mole ratio less than about 1:10 to the aminophenylhalide reactant, and preferably less than about 1:100. The minimum amount of palladium catalyst depends on other parameters, including the identity of the ligand, the concentration of the ligand, the reaction temperature, the reactivity of the specific reactants, how much of the aminophenylhalide reactant is the N-benzylidene aminophenylhalide, the concentration of the reactants, the solvent, and the maximum time allowed for completion of the reaction, and can be readily determined by routine experimentation. In typical embodiments, a suitable mole ratio of the palladium catalyst to the aminophenylhalide reactant is in the range of 1:10,000 to 1:100, preferably in the range 1:5000 to 1:500.

Suitable cuprous salts include those having the general formula CuA, wherein A is defined as above, but is independently selected. Preferred cuprous salts are the cuprous halides. Cuprous iodide is particularly preferred. The amount of cuprous salt is not critical, but should be a catalytic mole ratio less than about 1:10 to the aminophenylhalide reactant. The minimum amount of cuprous salt depends on other parameters, like those listed above for the amount of palladium catalyst. In typical embodiments, a suitable mole ratio of cuprous salt to palladium catalyst is in the range of 1:1 to 100:1, preferably in the range of 5:1 to 25:1.

The reaction of the aminophenylhalide reactant with the terminal acetylene may be conducted without solvent, with an excess of amine base as solvent, with an additional solvent that is reaction-inert, or with a mixture of excess amine base and a solvent that is reaction inert. By reaction-inert solvent is meant a solvent system which does not react with the reactants or products of the reaction, or react unfavorably with the catalyst. The term solvent system is used to indicate that a single solvent or a mixture of two or more solvents can be used. Representative solvents are aromatic hydrocarbons such as benzene, toluene, xylene; aliphatic hydrocarbons such as pentane, hexane, heptane; acetonitrile; dialkyl ethers; cyclic ethers, polar aprotic solvents such as dimethylformamide, dimethylacetamide, N-methylpyrollidone, and sulfolane, chlorinated hydrocarbons such as methylene chloride, dichloroethylene, carbon tetrachloride, and chloroform, and mixtures thereof. The solvent system used need not bring about complete solution of the reactants. Preferred solvents include the amine base and mixtures of the amine base and a hydrocarbon solvent.

The reaction temperature is not critical, but is preferably sufficient for the reaction to proceed at a practical rate. Suitable and optimal reaction temperatures depend on a number of other parameters, including the reactivity of the specific catalyst system, the concentration of the catalyst components, the concentrations and reactivities of the specific reactants, and the solvent, and can be readily determined by routine experimentation. In typical embodiments, the reaction is conducted at a temperature in the range from about 20° C. to 200° C., preferably from about 50° C. to 120° C. It is often convenient to conduct the reaction at the reflux temperature of the reaction mixture.

The order of addition of the reaction components is not critical. All the reaction components can be added prior to any heating to the reaction temperature, or one or more components may be added when the other components have be brought to the desired reaction temperature. The preferred order of addition for any specific embodiment can be determined by routine experimentation with a view towards both reaction performance and chemical engineering considerations.

N-benzylidene aminophenylacetylene formed by the reaction may be hydrolyzed to the aminophenylacetylene by methods known in the art for the hydrolysis of C,N-diaryl imines in general. Typically this is accomplished by treating the imine with water and an acid. The hydrolysis of the N-benzylidene aminophenylacetylene can be conducted at any point in the process subsequent to the conversion of the aminophenylhalide reactant being judged suitably complete. Water and acid can be added to the converted reaction mixture to effect the hydrolysis prior to any separations. Alternatively, the hydrolysis can conducted later in the separations scheme. Another alternative is to isolate the N-benzylidene aminophenylacetylene, optionally in combination with any free aminophenylacetylene co-product of the reaction, and subsequently subject it to hydrolysis to the aminophenylacetylene.

The N-benzylidene aminophenylacetylene and the aminophenylacetylene can each be recovered and isolated by known methods.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Example 1

Preparation of 3-(N-benzylylidene)aminophenylacetylene dimethylcarbinol:

A solution of equimolar amounts of 3-bromoaniline (1.72 g, 10 mmol) and benzaldehyde (1.06 g, 10 mmol), and benzoic acid (0.20 g, 1.6 mmol) in triethylamine (5 g) was heated at reflux for 12 hours. The reaction was essentially complete by thin-layer chromatography (40% ethyl acetate/heptane; silica). The $^1$H-NMR spectrum of an aliquot showed the presence of N-benzylidene 3-aminophenylbromide (benzylidenyl proton singlet at δ 8.43 ($CD_2Cl_2$); compared to authentic N-benzylidene aniline at 8.45).

The reaction mixture was cooled and $PdCl_2$ (2 mg, 0.01 mmol) and triphenylphosphine (73 mg, 0.28 mmol) were added. The mixture was deaerated by bubbling nitrogen. This reaction mixture was heated at reflux for 20 min and then treated with a slurry of CuI (20 mg, 0.1 mmol) in 2-methyl-3-butyn-2-ol (1.1 g, 13 mmol). The reaction mixture was heated at reflux for 12 hours. Thin-layer chromatography (40% ethyl acetate/heptane; silica) showed the reaction to be complete.

An aliquot of the reaction mixture was dissolved in $CH_2Cl_2$/hexane and extracted with water. The organic phase was evaporated under a stream of nitrogen. The $^1$H-NMR spectrum of the resulting oil was consistent with the benzylidene imine of 3-methyl-4-(3-aminophenyl)-3-butyn-2-ol (N-benzylidene 3-aminophenylacetylene dimethylcarbinol), having resonances for both the benzylidenyl proton (δ 8.46, s, 1H) and the dimethylcarbinol moiety (δ 1.60, s, 6H). $^1$H-NMR ($CD_2Cl_2$): δ 1.60 (s, 6H), 2.5 (brs, 1H), 7.15–7.20 (m, 1H), 7.25–7.49 (m, 3H), 7.45–7.55 (m, 3H), 7.88–7.95 (m, 2H), 8.46 (s, 1H).

Another aliquot of the reaction mixture was partitioned between 40% ethyl acetate/heptane and water. The organic phase was analyzed by GC/MS, showing only one major non-solvent peak. The mass spectrum of this elute showed a molecular ion (M+) of mass 263, consistent with $C_{18}H_{17}NO$ for N-benzylidene 3-aminophenylacetylene dimethylcarbinol.

Another aliquot of the reaction mixture was hydrolyzed to remove the N-benzylidene group by partitioning between 40% ethyl acetate/heptane and aqueous HCl. The acidic aqueous phase was separated, basified with aqueous sodium hydroxide, and extracted with 40% ethyl acetate/heptane. Thin-layer chromatography of the organic solution showed (vs. authentic standard) 3-methyl-4-(3-aminophenyl)-3-butyn-2-ol as the major component.

This example illustrates the process of the present invention wherein a N-benzylidene aminophenylacetylene (N-benzylidene 3-aminophenylacetylene dimethylcarbinol) is prepared by reacting a N-benzylidene aminophenylhalide (N-benzylidene 3-aminophenylbromide), preformed ex situ, with a terminal acetylene (2-methyl-3-butyn-2-ol; also called acetylene dimethylcarbinol) in the presence of a base (triethylamine) and a catalyst system comprising a palladium catalyst and a cuprous salt.

Example 2

Preparation of 3-aminophenylacetylene dimethylcarbinol:

To a nitrogen purged 250 mL three-neck flask equipped with a mechanical stirrer, reflux condenser and septum inlet was added benzoic acid (300 mg, 2.8 mmol) and $PdCl_2$ (25 mg). Then 3-bromoaniline (25 g, 145 mmol), benzaldehyde (4.6 g, 44 mmol) and triethylamine (80 mL) were charged. The resulting mixture was vacuum deaerated (150 torr; $N_2$ backfill; 5x) and heated under nitrogen at reflux for one hour to form the N-benzylidene 3-aminophenylbromide.

The resulting mixture was cooled to 50° C. and triphenylphosphine (0.94 g in 10 mL triethylamine) was added via syringe. Then 2-methyl-3-butyn-2-ol (16 g) was added followed by CuI (0.3 g in 20 mL triethylamine). The reaction mixture was refluxed for 10 hours. After cooling, toluene (20 mL) and water (40 mL) containing 50% sodium hydroxide (11.6 g) were added. The aqueous phase was separated and the resulting mixture was distilled under vacuum (200 torr) while adding more toluene (3x, 75 mL). A total of 300 mL of distillate was obtained. The resulting slurry was cooled and treated with HCl (100 mL, containing 21 g of 37% HCl). This mixture was stirred for 1 hour at room temperature to hydrolyze the N-benzylidene 3-aminophenylacetylene dimethylcarbinol.

The aqueous solution of the product was separated and treated with toluene (35 mL) and ethyl acetate (30 mL). This mixture was cooled (ice bath) and basified with 50% sodium hydroxide (17 g). Some of the aqueous phase was separated and then the mixture was heated to 60° C. The remaining aqueous phase was separated and more toluene (155 mL) was added. This mixture was cooled to crystallize the product. Filtration and washing with cold toluene and drying in vacuo afforded 19.21 g (75.5%) of 2-methyl-4-(3-aminophenyl)-3-butyn-2-ol. $^1$H-NMR (DMSO-d6): δ 1.44 (s, 6H), 5.14 (brs, 2H), 5.37 (s, 1H), 6.5–6.7 (m, 3H), 6.97 (t, 1H, J=7.8Hz).

This example illustrates the process of the invention wherein a mixture of an aminophenylhalide and a corresponding N-benzylidene aminophenylhalide, preformed ex situ by reacting the aminophenylhalide with a substoichiometric amount of a benzaldehyde (0.3 eq in this case), are reacted with a terminal acetylene in the presence of a base and a catalyst system comprising a palladium catalyst and a cuprous salt to provide a mixture of the aminophenylacetylene and the corresponding N-benzylidene aminophenylacetylene, and hydrolyzing the N-benzylidene aminophenylacetylene in the mixture to the aminophenylacetylene.

Comparative Example

The procedure was the same as in Example 2 using benzaldehyde free of benzoic acid, through the steps intended for the ex situ formation of the N-benzylidene 3-aminophenylbromide and the catalyzed reaction with 2-methyl-3-butyn-2-ol, with the exception that no benzoic acid was added. Upon the addition of the CuI, an apparent precipitation of Pd was observed (not seen in the procedure of Example 2). After several hours of reflux no reaction to form an aminophenylacetylene dimethylcarbinol, with or without the N-benzylidene moiety, could be observed by thin-layer chromatography.

Comparison with Examples 2 demonstrates that when the N-benzylidene imine of the aminophenylhalide is not present, in this case because no acid catalyst was provided for its formation from the benzaldehyde, the catalytic reaction to couple the aminophenylhalide with the terminal acetylene does not readily proceed. It further indicates that, in the present invention, the availability of the N-benzylidene aminophenylhalide for reaction serves to stabilize the palladium catalyst.

Example 3

Preparation of 3-aminophenylacetylene dimethylcarbinol:

A mixture of 4-bromoaniline (1.72 g, 10 mmol), benzaldehyde (0.27 g free of benzoic acid, 2.5 mmol), benzoic acid (20 mg, 0.16 mmol), $PdCl_2$ (2 mg) and triethylamine (3.5 g) was deaerated by bubbling nitrogen and then heated to reflux for 30 min. The reaction mixture was cooled to 50° C. and treated with triphenylphosphine (73 mg in 0.5 g of TEA) followed by 2-methyl-3-butyn-2-ol (1.1 g, 13 mmol) and then CuI (20 mg in 1 g TEA). This mixture was heated at reflux for 12 hr. Thin layer chromatography showed the reaction to form 3-aminophenylacetylene dimethylcarbinol, in mixture with N-benzylidene 3-aminophenylacetylene dimethylcarbinol, to be complete.

Comparison to the Comparative Example above demonstrates that the addition of an acid catalyst (in this case benzoic acid) in order to form the N-benzylidene aminophenylhalide when using benzaldehyde free of benzoic acid provides for a successful conversion of the aminophenylhalide, in mixture with the N-benzylidene aminophenylhalide, to the aminophenylacetylene, in mixture with the N-benzylidene 3-aminophenylacetylene.

Example 4

Preparation of 3-aminophenylacetylene dimethylcarbinol:

A mixture of 3-bromoaniline (1.72 g, 10 mmol), 2-methyl-3-butyn-2-ol (1.1 g, 13 mmol), benzaldehyde (0.3 g, 2.8 mmol, containing some benzoic acid impurity), triethylamine (3 g), toluene (3 g), dichlorobis(triphenylphosphine)palladium (15 mg), and triphenylphosphine (80 mg) was deaerated by bubbling nitrogen and heated to 80° C. and treated with CuI (10 mg). This mixture was refluxed for 7 hours. The cooled reaction mixture was treated with aq NaOH (3 mL, 5 mM). The aqueous phase was separated and the organic phase was distilled to remove TEA with more toluene being added. The resulting toluene solution was treated with aq HCl (5 mL, 9%). After 30 min the aqueous phase was separated and basified with 50% NaOH. The precipitated solid was filtered and dried to afford 1.2 g of 3-aminophenylacetylene dimethylcarbinol.

This example demonstrates that the N-benzylidene aminophenylhalide need not be preformed ex situ, but can be formed in situ from the aminophenylhalide and the benzaldehyde, in this case substoichiometric benzaldehyde containing benzoic acid impurity.

Example 5

Preparation of 3-aminophenylacetylene dimethylcarbinol:

A mixture of 3-bromoaniline (1.72 g, 10 mmol), 2-methyl-3-butyn-2-ol (1.1 g, 13 mmol), 3-nitrobenzaldehyde (0.5 g, 3.3 mmol), triethylamine (5 g), dichlorobis(triphenyl-phosphine)palladium (15 mg) and triphenylphosphine (80 mg) was deaerated by bubbling nitrogen. The reaction mixture was heated to 80° C. and treated with CuI (10 mg). After 7 hr at reflux thin-layer chromatography showed nearly complete conversion of the 3-bromoaniline to a mixture of 3-aminophenylacetylene dimethylcarbinol and N-(3-nitrobenzylidene) aminophenyl acetylene dimethylcarbinol.

This example demonstrates the use of another benzylidene group in the process of the invention, in this case 3-nitrobenzylidene provided by a substoichiometric amount of 3-nitrobenzaldehyde with in situ formation of the N-(3-nitrobenzylidene) aminophenylhalide.

Example 6
Preparation of 3-aminodiphenylacetylene:

A mixture of 3-bromoaniline (1.72 g, 10 mmol), benzaldehyde (0.27 g, 2.5 mmol, containing some benzoic acid), and PdCl$_2$ (2 mg) in triethylamine (4 g) was deaerated by bubbling nitrogen. This mixture was refluxed for 45 min, then cooled to 50° C. and treated with triphenylphosphine (73 mg in 0.8g triethylamine). Phenyl-acetylene (1.33 g, 13 mmol) and CuI (25 mg in 0.8 g triethylamine) were then added. After refluxing for 6 hr, the reaction mixture was cooled and treated with water (5 mL). The triethylamine layer was concentrated in vacuo and replaced by toluene. To this solution was added aqueous HCl (15 mL, 7%). A precipitate was formed and it was filtered and washed with toluene. Drying in vacuo afforded 3-aminodiphenylacetylene hydrochloride (1.4 g).

This example demonstrates another terminal acetylene in the process of the invention. Phenylacetylene is used to make an aminodiphenylacetylene.

Example 7
Preparation of 5-(4-aminophenyl)-4-pentyn-1-ol:

A mixture of 4-bromo-aniline (1.72 g, 10 mmol), benzaldehyde (0.27 g, 2.5 mmol), benzoic acid (0.05 g, 0.4 mmol), PdCl$_2$ (2 mg) and triethylamine (3.5 g) was deaerated by bubbling nitrogen and then heated to reflux for 45 min. Thin-layer chromatography showed the formation of N-benzylidene 4-aminophenylbromide). The reaction mixture was cooled to 50° C. and treated with triphenylphosphine (73 mg in 1 g of triethylamine) followed by a slurry of CuI (20 mg) and 4-pentyn-1-ol (1.1 g, 13 mmol). This reaction mixture was heated at reflux for 10 hr. The mixture was cooled and diluted with triethylamine (5 mL) and treated with water (6 mL). The aqueous layer was separated and the triethylamine layer was concentrated under vacuum. Toluene was added and the mixture again concentrated. Then aqueous HCl (10 mL, 7%) was added. The resulting aqueous solution was cooled, basified with 50% NaOH, and extracted with ethyl acetate. The ethyl acetate extract was evaporated under vacuum and the residue was flash chromatographed (20% ethyl acetate-dichloromethane, silica) to yield 0.57 g of 5-(4-aminophenyl)-4-pentyn-1-ol as an oil.

This example demonstrates the use of another aminophenylhalide, 4-bromoaniline, and another terminal acetylene, 4-pentyn-1-ol, in the process of the invention.

Example 8
Preparation of 3-aminophenylacetylene dimethylcarbinol:

A mixture of 3-bromoaniline (1.72 g, 10 mmol), 2-methyl-3-butyn-2-ol (1.1 g, 13 mmol) and benzaldehyde (0.3 g, , 2.8 mmol, containing some benzoic acid) in triethylamine (5 g) was treated with palladium diacetate (11 mg) and triphenylphosphine (197 mg). This mixture was deaerated by bubbling nitrogen and then heated to reflux. CuI (10 mg) was added and the mixture was heated at reflux for 7 hours. Product isolation analogous to Example 2 gave 1.2 g of 3-aminophenylacetylene dimethylcarbinol.

This Example demonstrates the use of another palladium salt, palladium diacetate, to provide the palladium catalyst in the present invention.

The present invention has been shown by both description and examples. The Examples are only examples and cannot be construed to limit the scope of the invention. One of ordinary skill in the art will envision equivalents to the inventive process described by the following claims which are within the scope and spirit of the claimed invention.

I claim as my invention:

1. An N-benzylidene aminophenylacetylene carbinol selected from cis isomers and trans isomers, and mixtures thereof, about the carbon nitrogen double bond.

2. The N-benzylidene aminophenylacetylene carbinol of claim 1 wherein the trans isomer has the formula

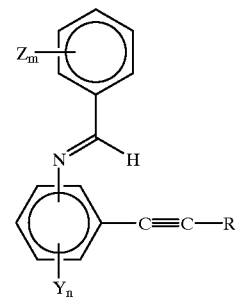

wherein
Y and Z are substituents independently selected from fluoro, chloro, alkyl, alkenyl, alkynyl, alkoxy, acyloxy, aryl, aryloxy, heteroaryl, OH, NO$_2$, CN, COOH, SO$_2$R, SOR, NH$_2$, NH-alkyl, N-dialkyl, trihalomethyl, NHCO-alkyl, CONH-alkyl, CON-dialkyl, COO-alkyl, CONH$_2$, CO-alkyl, NHCOH, NHCOO-alkyl, CO-aryl, COO-aryl, CHCHCO$_2$-alkyl, CHCHCO$_2$H, PO-diaryl, and PO-dialkyl;

n is an integer from 0 to 4, wherein when n is greater than 1, the Y substituents may be the same or different and are selected independently of each other;

m is an integer from 0 to 5, wherein when m is greater than 1, the Z substituents may be the same or different and are selected independently of each other;

and R is an alpha-hydroxy alkyl group.

3. The compound of claim 2 comprising a N-benzylidene aminophenylacetylene carbinol wherein R is an alpha-hydroxy alkyl group of the formula —C(OH)R'R" wherein R' and R" are independently selected from hydrogen lower alkyl groups having from 1 to 4 carbon atoms, phenyl, substituted phenyl; or R' and R" when taken together with the carbon bearing the hydroxyl group form a cyclohexyl or cylopentyl group.

4. The compound of claim 3 wherein the N-benzylidene aminophenylacetylene carbinol is N-benzylidene 3-aminophenylacetylene dimethylcarbinol.

\* \* \* \* \*